(12) United States Patent
Couzan et al.

(10) Patent No.: US 6,216,495 B1
(45) Date of Patent: Apr. 17, 2001

(54) SUPPORT STOCKING

(75) Inventors: Serge Couzan, Saint-Etienne; Michael Prufer, Beausoleil, both of (FR)

(73) Assignee: BV Sport, Fontaine (FR)

(*) Notice: Subject to any disclaimer, the term of this patent is extended or adjusted under 35 U.S.C. 154(b) by 0 days.

(21) Appl. No.: 09/284,653

(22) PCT Filed: Oct. 22, 1997

(86) PCT No.: PCT/FR97/01892

§ 371 Date: May 13, 1999

§ 102(e) Date: May 13, 1999

(87) PCT Pub. No.: WO98/18418

PCT Pub. Date: May 7, 1998

(30) Foreign Application Priority Data

Oct. 25, 1996 (FR) .................................................. 96 13296

(51) Int. Cl.$^7$ ....................................................... D04B 9/46
(52) U.S. Cl. .......................... 66/183; 66/178 R; 602/63; 2/239
(58) Field of Search ................................. 66/178 R, 183, 66/184, 178 A; 2/240, 54, 409, 242; 602/62, 63

(56) References Cited

U.S. PATENT DOCUMENTS

| 3,386,270 | | 6/1968 | Simmons . | |
|---|---|---|---|---|
| 4,502,301 | * | 3/1985 | Swallow et al. | 66/178 |
| 4,745,917 | | 5/1988 | Hasty et al. . | |

FOREIGN PATENT DOCUMENTS

| 602 653 | 9/1934 | (DE) . |
|---|---|---|
| 24 13 332 A1 | 9/1975 | (DE) . |
| 38 32 798 A1 | 3/1990 | (DE) . |
| 0 553 615 A1 | 8/1993 | (EP) . |
| 1124593 | 10/1956 | (FR) . |
| 1445233 | 8/1976 | (GB) . |
| 2 213 386 | 8/1989 | (GB) . |

* cited by examiner

*Primary Examiner*—Danny Worrell
(74) *Attorney, Agent, or Firm*—Oliff & Berridge, PLC

(57) ABSTRACT

A support stocking having an elastic compression force on the calf greater than the compression force on the ankle and foot of a person. The compressive forces of the support stocking aid in venous recovery after physical exertion, such as in sports or athletics. The support stocking's design also aids in delaying problematic venous conditions such as venous insufficiency, even in non-athletes.

4 Claims, 1 Drawing Sheet

SUPPORT STOCKING

BACKGROUND OF THE INVENTION

The invention relates to a support stocking designed for sports and sportsmen.

The elastic compression has proven its effectiveness in the-treatment of venous insufficiency, particularly in the early stages. It also makes it possible to slow the development into chronic venous insufficiency which occurs progressively and most often over several years.

Sport is theoretically beneficial to venous return, but only under certain conditions, which are rarely encountered in routine or competitive practice. For example, the type of sport, its intensity, its duration, the level of physical conditioning of the sportsmen, lack of training and insufficient recovery time may have an effect on the venous condition and be responsible for a loss of performance or the occurrence of injuries, such as strains, torn muscles, periostitis, chronic tendinitis or torn Achilles tendons.

There are few studies on the role of sport and compression on the venous system, and the results sometimes disagree. Nevertheless, the physical principles and hemodynamic effects of compression demonstrate its beneficial results when it is applied to sportsmen during and after physical activity.

The elastic supports currently available, with a measurable pressure, are reserved only for patients suffering functional or organic venous insufficiency. The pressures have been adapted as a function of parameters relating to the venous insufficiency. However, all these parameters and the hemodynamic conditions are different for sportsmen without venous insufficiency.

SUMMARY OF THE INVENTION

The object of the present invention is to adapt the support stockings obtained by various knitting methods to obtain pressures specific to sportsmen and to the practice of sport, while accommodating their specific physiology.

The supports intended to correct venous insufficiency consist of stockings, leg stockings or knee-high stockings, thigh supports and knitted tights, comprising textile yarns combined with covered or uncovered elastic yarns of natural or synthetic origin. The tension imparted to the elastic yarns during knitting determines the compressive pressure, that is to say the radial force of retention on the leg. The knitting may be circular or linear and the elasticity may be in one or more directions. These support stockings can be manufactured in standard sizes or to measure.

In practice, the compression provided by the stocking is defined by a blood pressure measured in mm of mercury, according to the French standards (A.F.N.O.R.), and distinction is made, amongst other things, between a force I, generating a pressure of between 10 and 15 mm of mercury, a force II, generating a pressure of between 15.1 and 20 mm of mercury, and a force III, generating a pressure of between 20.1 and 36 mm of mercury. In the other European countries, these values differ and are 13 to 22 mm of mercury for class I, 23 to 33 mm of mercury for class II and 34 to 47 mm of mercury for class III.

In stockings or knee-high stockings correcting venous insufficiency, the compression force in a maximum on the foot and the ankle and decreases up to the calf or thigh. This is the case with the stockings described in U.S. Pat. No. 4,745,917. The impetus for this principle is that, whatever the etiology or the mechanisms responsible for the venous insufficiency reflux, stasis, hypertension, etc.), the effect on the veins is always localized primarily at the ankle, the foot or the lower third of the leg. FR-A-1,124,593 describes a stocking which, specifically, provides maximum compression over the lower third of the leg.

It is difficult to calculate therapeutic compressive pressures because a number of factors are involved: the position of the body, the anatomical and biomechanical condition of the muscles, joints, tissues, the anatomical state of the venous and perivenous structures, the force of gravity, the tissue pressures, the hemodynamics and the venous pressures when changing position, under exertion, according to the variations in cardiac and abdominal pressures, the venous flow and reflux rates (deep, superficial, intermediate, etc.). Only some of the above factors are measurable.

Prior work has established a principle of graduating the compressive pressures in the downward direction, the maximum pressure being level with the ankle and the minimum pressure (=0) level with the heart. This maximum pressure at the ankle is calculated on the basis of data relating to the physiology of the venous insufficiency accompanied by venous reflux and hyperdiatension. This may not be applicable to sportsmen without venous insufficiency, whose physiology is different and specific.

This is why the applicants have tried to define new blood pressures and new gradients from studying the physiology of venous return and compression in sportsmen without venous insufficiency, during and following exertion.

An overview of physiopathology would seem essential for explaining the decisive elements of the present invention.

The main physiological parameters involved with sportsmen in the practice of sport are represented by venous hyperdistension with an increase in the oxygen-depleted residual volume (up to 50% of the basic volume) an increase in the caliber of the veins (30 to 40% for prolonged or intense exertion), and by an increase in the tranamural venous pressure. The results from the literature relating to measurments of the venous pressures and pressure variations during or following exertion disagree depending on the methodology because, most often, the measurements are taken at the ankle level. This may not correspond to the maximum pressure because sportsmen without venous insufficiency do not exhibit valvular reflux, have good articulation and an efficient plantar and muscular venous pump. The venous filling and dilation will firstly affect the muscles of the calf and have the superficial venous network, then the perforans and the deep network. Venous hypertension will therefore tend to be a maximum at the calf level.

It is also of interest to examine plantar vein physiology, applied to sportsmen.

The plantar venous axes are directly connected to the posterior tibial veins and also communicate with the superficial veins of the back of the foot through the perforans, some of which are of large caliber. The plantar venous reservoir ejected on each step can be estimated at between 30 and 40 ml. During the diastole, three antireflux mechanisms are involved: the valvules, of which there are many on the confluences and the collectors; a plexal device of the venous confluences which form a substantial barrier and a fibrous tunnel which surrounds the veins most highly exposed to the reflux.

This antireflux device is thus effective in sportsmen without venous insufficiency due to valvular incontinence. There is therefore no need to compress the foot and the malleolar region too much in sportsmen. This is of benefit both in physical terms Laplace's law) and in terms of tolerance to the support, since compression of the foot and the malleoli is hardest to endure. It should be added to this that, with the improvement in the podological characteristics of most sports shoes, the ejection conditions of the plantar venous reservoir are optimal.

The support stocking for the practice of sports, according to the invention, is composed of a sheet, elastically deformable in at least one direction, which is configured, when the stocking is being made, for example by stitching its edges or circular knitting, so as to exert on the body, that is to say at least on the foot and the leg, compressive pressures which are different between the foot and the leg.

According to the invention, the part of the stocking that extends from the end of the foot to just above the malleoli and sheaths the foot and the ankle is structured so as to exert a compressive pressure P1 with a value less than that of the compressive pressure P2 exerted by the part of the stocking sheathing the calf.

With this stocking, the compression exerted on a sportsman is therefore moderate at foot level up to the malleoli and is stronger on the calf, and therefore contrasts with the compression used for treating venous insufficiency, which for its part decreases upward while firmly retaining the foot and the ankle, where it is at a maximum.

This compression, applied to sportsmen, provides the following hemodynamic effects;

a) improvement in the function of the venous pump of the calf by increasing the venous flush volume by 20 to 50%, decreasing the residual volume, increasing the venous filling time after exercise and improving the right cardiac filling, b) decrease in the venous pressure and increase in the venous flow rate, leading to an effect of decongesting the muscles and the tissues, c) decrease in the caliber of the superficial and deep veins, promoting return of the valvules moved away during the distension on the wall occurring during exertion. This gives the possibility of restoring incompetent valvular function. The consequences are reduction in the accumulation of the oxygen-depleted venous blood in the calf, reducing stasis and hypoxia and promoting the elimination of waste. A metabolic effect is produced with better muscle, tendon and tissue oxygenation, thus reducing the risk of inflammation and all its pathogenic consequences, d) the effects on the microcirculation are represented by an increase in the cutaneous distribution and an improvement in the veno-arterial reflex. The possibility of regression of parietal impairment and reversibility of medial dysplasia when applying the compression early have also been observed, e) wearing a support regularly gives the sportsman the benefit of a remanent effect, providing continuation of the haemodynamic effects after this support has been removed, as has been observed following continuous wearing of a support for venous insufficiency.

In one embodiment of the invention, and when the sheath contains elastic yarns whose knitting tension determines the compressive pressure, each stocking is divided, by a fictitious line, extending from the Achilles tendon to the instep and passing over the malleoli, into a lower part that sheaths the foot and the ankle and in which the elastic yarns exert a tension providing a pressure P1, and an upper part that extends from below the malleoli to below the knee and sheaths the calf and the leg, in which the elastic yarns exert a tension providing, at least on the calf, a pressure P2 higher than the pressure P1.

In the stocking according to the invention, since the maximum pressure force is localized at the calf level and in accordance with hemodynamic data, it is not essential to create downward graduation. Indeed, and unlike support stockings for those with venous insufficiency, the pressure at the upper part of the calf should be strong enough to act on the superficial, muscular and deep venous network, without exerting a tourniquet or constricting effect. This is particularly important for the specific made-to-measure compression applied to high-level sportsmen, because it is necessary to obtain, to the greatest possible extent by the "aponeurosis effect", the function of an extra muscle improving performance and, by the sturbo effect, better oxygenation of the muscle fiber, during and following exertion, making it possible to assist recovery and reduce the risk of inflammation.

However, for less advanced sportsmen and to facilitate manufacture on knitting machines, it is possible to maintain a downward graduation, but while still keeping, at the calf level, a pressure higher than the pressure exerted on the ankle and the foot, which distinguishes the support for a sportsman from the support for an individual with venous insufficiency.

The principal characteristic of the invention is to apply to support stockings for sportsmen pressures and pressure gradients which are different and opposite to stockings for those with venous insufficiency, without producing a tourniquet effect.

When such a stocking is being worn, the elastic support included in the stocking acts in compression and promotes venous return and liquid movements to the left heart, decreases venous stasis, facilitates the elimination of acid metabolites and thus allows better oxygenation of the muscle fiber (turbo effect). The combination of the support and the compression is most effective during muscle action, because it reinforces the effects of muscle contraction, behaving as an extra muscle (aponeurosis effect).

BRIEF DESCRIPTION OF THE DRAWING

Other characteristics and advantages will emerge from the following description with reference to the appended schematic drawing.

DETAILED DESCRIPTION OF THE PREFERRED EMBODIMENTS

Figure 1:
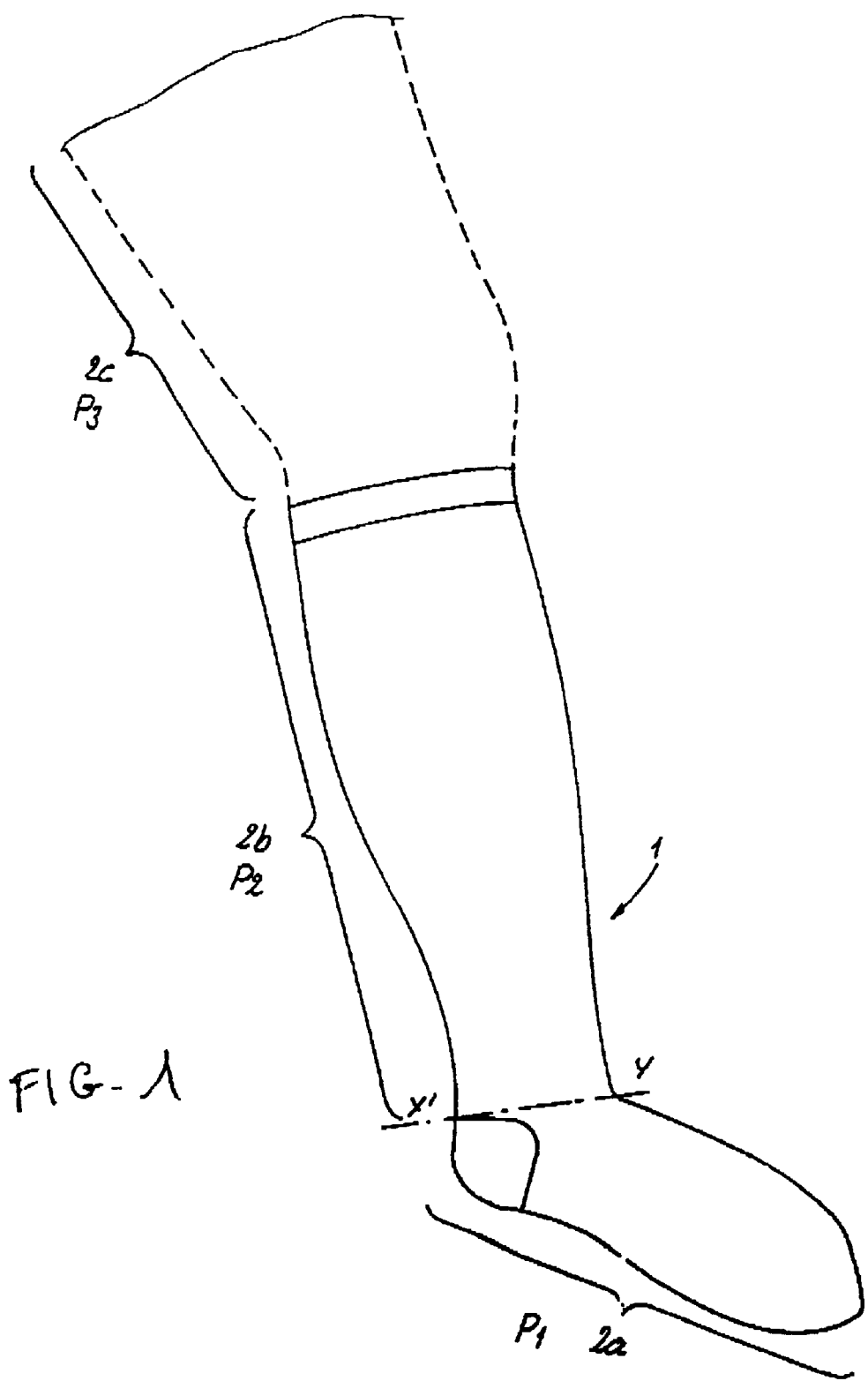
FIG. 1 is a side view, a leg stocking according to the invention, the sheath of which is obtained by knitting.

This leg stocking 1 is divided on either side of the line y'–y, represented by dots and dashes, extending from the Achilles tendon to the instep and passing over the malleoli, on the one hand, into a lower part 2a sheathing the foot and the ankle and, on the other hand, into an upper part 2b stopping under the knee and sheathing the leg and, above all, the calf. In the case of a thigh stocking or tights, the part 2b is continued by an additional part 2c sheathing the thigh. These parts which, in the known way, are produced by knitting on a knitting loom followed by a weave and conditions well known to the person skilled in the art manufacturing support stockings for the treatment of venous insufficiency, differ from the latter by the values of the tension given to the elastic yarns defining the compression. Any knitting or weaving process and any materials capable of imparting these tension values may be used.

In one embodiment of the invention, relating more particularly to sports involving low venous risk and beginnerand intermediate-level sportsmen, the values of the compressive pressures, respectively P1 in the lower part 2a, P2 in the upper part 2b, and where appropriate P3 in the additional part 2c are indicated in the table below.

|  | Lower part 2a P1 | Upper part 2b P2 | Additional part 2c P3 |
| --- | --- | --- | --- |
| Value of th pressure | | | |
| in mm Hg | 7 to 13 | 15 to 25 | 7 to 13 |
| in pascals | 920 to 1710 | 1973 to 3289 | 920 to 1710 |
| Reference value | | | |
| in mm Hg | 10 | 20 | 10 |
| in pascals | 1315 | 2631 | 1315 |

It will be noted that, in thigh stockings or tights, the value P3 is of the same order as the value of P1.

In the part 2b sheathing the leg, there is no need of downward graduation, the pressure P2 remaining the same from top to bottom. However, for ease of knitting, since machines are adjusted to provide graduation, it is possible to keep downward graduation, but on condition that the pressure P2 exerted at the calf level is always higher than the pressure P1 exerted at foot and ankle level, this being in order to accommodate the above-described venous physiology specific to sportsmen.

For high-level sportsmen or sports involving a risk to the veins exerting significant stresses on the venous return, such as abrupt acceleration or deceleration (motor sport, formula 1, aerobatics, etc.) or prolonged Valsalva maneuvering (weight lifting, body building, etc.), the compressive pressures will be determined on a case by case basis. In this embodiment of the invention, the tension imparted to the elastic yarns keeps the value gradients according to the invention with pressures P1 at the foot and ankle level in the part 2a always less than those P2 applied at the calf level. In the case of thigh stockings or tights, the tension imparted to the elastic yarns in the additional part 2c provides a compressive pressure P3 identical or similar to that P1 on the foot and the ankle, and in any event less than P2. In order not to exert a tourniquet effect, the pressure P2 exerted at the calf level should not be more than three times the value of the pressure P1 exerted at the foot and ankle level.

In one variant (not shown) each stocking is made from simple or complex extensible layers which are structured, that is to say cut and stitched or bonded to one another to form a sheath comprising the parts 2a, 2b and, where appropriate, 2c which, when they are on the body, provide the compressive pressures defined above.

The stocking according to the invention should, of course, be worn during exertion and then immediately after exertion to improve recovery, especially in the event of lengthy traveling or standing after exertion.

In certain standard cases, depending on tolerance, the differential compression provided by each stocking is doubled, after exertion, by putting over the first stocking a second stocking which is identical to the first, which accelerates recovery.

A clinical study carried out on sportsmen, confidentially using leg stockings according to the invention showed that the results provided by this leg stocking were beneficial after exertion, during the recovery period, and also during exertion.

During exertion, all the clinical signs, and more particularly edema, regress. As regards the other signs, the improvements were as follows:

sluggishness and fatigue 86%, cramp 89%, diesthesia 71%.

The compression also significantly reduced the duration of the clinical signs and eased recovery. With sportsmen carrying out timed or graded tests, an improvement in physical performance was observed in 88% of cases. Compression was judged beneficial to pain occuring as a consequence of inflammation or muscle or tendon incidents in 83% of cases.

Following exertion, the effectiveness of the compression was maximal. This period, which in theory corresponds to A recovery phase, is ignored by most sportsmen. Very often, stretching or massage are not or cannot be carried out and the period which follows the exertion accentuates the venous stasis (standing, prolonged sitting, etc.). Compression, although not replacing these recovery techniques, is an excellent supplement and is equivalent to pressure therapy or one night of rest, when it is worn for at least two hours following the exertion. In the context of this study, it was found that all the clinical signs were improved by wearing the support during this recovery phase. Most frequent were the feeling of sluggishness or fatigue, which disappeared in 97% of cases, twinges in 93% of cases, cramp in 98% of cases, and diesthesia in 100% of cases. Less significantly, because they were not a great problem and were too rare in the sample examined, improvements were observed in edema and phlebalgia.

In most standard cases, better recovery was provided when, following exertion, the sportsman put a second leg stocking, identical to the first, on each leg, which had the effect of reducing the stasis volume, reducing the caliber of all the veins and significantly accelerating the return rate, and consequently the removal of oxygen-depleted blood.

Although beneficial for high-level sportsmen, the stocking according to the invention is also aimed at those engaging in sports on an everyday or even occasional basis, because by improving performance and muscular recovery (with a reduction in the periods of fatigue), it reduces the risks to the veins in the long term. In sports defined as entailing this risk, it compensates for venous insufficiency known or as yet undetected, and delays venous conditions.

What is claimed is:

1. A support stocking comprising:
    a sheath that extends from the foot to the leg, wherein the stocking is elastically deformable in at least one direction and configured to exert on the body a compressive pressure having different values on the foot and on the leg, wherein a first part of the stocking extends from the end of the foot to just above the malleoli and sheaths the foot and the ankle to exert a first compressive pressure with a value less than that of a second compressive pressure exerted by a second part of the stocking sheathing the calf, the compressive pressure being graduated downward between the second pressure and the first pressure.

2. The stocking as claimed in claim 1, wherein the sheath contains elastic yarns whose knitting tension determines the compressive pressure, each stocking is divided, by a fictitious line, extending from the Achilles tendon to the instep and passing over the malleoli, into the first part that sheaths the foot and the ankle and in which the elastic yarns exert a tension providing the first pressure, and the second part that extends from below the malleoli to below the knee and sheaths the calf and the leg, in which the elastic yarns exert a tension providing, at least on the calf, the second pressure higher than the first pressure.

3. The stocking as claimed in claim 2, wherein the stocking comprises a third part that continues the second part and extends over the thigh, the tension imparted to the elastic yarns of the third part provides a third compressive pressure having a value of the same order as that of the first pressure exerted on the first part.

4. The stocking as claimed in claim 1, wherein the first compressive pressure has a value of between 920 and 1710 pascals, while the second compressive pressure exerted on the calf has a value of between 1973 and 3289 pascals.

* * * * *